US009157065B2

(12) United States Patent
Buniatian et al.

(10) Patent No.: US 9,157,065 B2
(45) Date of Patent: Oct. 13, 2015

(54) USE OF THE OPPOSITE CELL DIFFERENTIATION PROGRAM (OCDP) FOR THE TREATMENT OF DEGENERATED ORGANS IN THE PATHOLOGICAL STATE

(75) Inventors: Gayane Buniatian, Tubingen (DE); Rolf Gebhardt, Leipzig (DE); Christoph Gleiter, Tubingen (DE); Lusine Danielyan, Tubingen (DE); Barbara Proksch, Tubingen (DE)

(73) Assignee: Universitat Leipzig (DE)

( * ) Notice: Subject to any disclaimer, the term of this patent is extended or adjusted under 35 U.S.C. 154(b) by 545 days.

(21) Appl. No.: 12/678,446

(22) PCT Filed: Apr. 18, 2008

(86) PCT No.: PCT/EP2008/003146
§ 371 (c)(1),
(2), (4) Date: Jun. 29, 2010

(87) PCT Pub. No.: WO2009/036817
PCT Pub. Date: Mar. 26, 2009

(65) Prior Publication Data
US 2010/0278786 A1    Nov. 4, 2010

(30) Foreign Application Priority Data
Sep. 18, 2007  (DE) .......................... 10 2007 044 487

(51) Int. Cl.
*A01N 63/00*  (2006.01)
*C12N 5/079*  (2010.01)
*A61K 35/12*  (2015.01)

(52) U.S. Cl.
CPC .............. *C12N 5/0622* (2013.01); *A61K 35/12* (2013.01); *C12N 2502/14* (2013.01)

(58) Field of Classification Search
None
See application file for complete search history.

(56) References Cited

U.S. PATENT DOCUMENTS

| 6,586,015 | B1 * | 7/2003 | Gebhardt et al. ............. 424/725 |
| 2002/0016002 | A1 * | 2/2002 | Toma et al. .................... 435/368 |
| 2004/0063202 | A1 * | 4/2004 | Petersen et al. ............... 435/368 |
| 2005/0169902 | A1 * | 8/2005 | Borlongan et al. ......... 424/93.71 |
| 2007/0128174 | A1 * | 6/2007 | Kleinsek et al. .............. 424/93.7 |
| 2007/0259825 | A1 * | 11/2007 | Rothstein et al. ............... 514/44 |
| 2008/0145342 | A1 * | 6/2008 | Qian et al. .................... 424/93.7 |
| 2010/0021386 | A1 * | 1/2010 | de la Monte et al. .......... 424/9.2 |
| 2011/0081323 | A1 | 4/2011 | Kleinsek et al. |

FOREIGN PATENT DOCUMENTS

| JP | 2006-508648 A | 3/2006 |
| JP | 2009-508650 A | 3/2009 |
| WO | WO-01/30981 A1 | 5/2001 |
| WO | WO-2004/020601 A2 | 3/2004 |
| WO | WO-2006/134602 A2 | 12/2006 |
| WO | WO-2007/025306 A1 | 3/2007 |
| WO | WO 2007/035843 * | 3/2007 ............. A61K 35/14 |
| WO | WO-2009036817 A1 | 3/2009 |

OTHER PUBLICATIONS

Mann et al., Gut, 50: 891-896 (2002).*
Buniatian et al., Biology of the Cell, 91:675-684 (1999).*
Morini et al., Abstract (2005).*
Buniatian et al., Neurochem. Intl., 38:373-383 (2001).*
Carotti et al., Liver Trans. 14:806-814 (2008).*
"Russian Application No. 2010114665/15(020715), English Translation of Office Action "Notification" mailed Feb. 17, 2012", 7 pgs.
"International Application No. PCT/EP2008/003146, International Preliminary Report on Patentability mailed Apr. 1, 2010", 9 pgs.
"International Application Serial No. PCT/EP2008/003146, International Search Report mailed Sep. 5, 2008", 8 pgs.
"International Application Serial No. PCT/EP2008/003146, Written Opinion mailed Sep. 5, 2008", 7 pgs.
Buniatian, G. H., et al., "Glial fibrillary acidic protein-positive cells of the kidney are capable of raising a protective biochemical barrier similar to astrocytes: expression of metallothionein in podocytes.", *Anat Rec.*, 267(4), (Aug. 1, 2002), 296-306.
Buniatian, Gayane Hrachia, et al., "Acquisition of blood—tissue barrier—supporting features by hepatic stellate cells and astrocytes of myofibroblastic phenotype. Inverse dynamics of metallothionein and glial fibrillary acidic protein expression", *Neurochemistry International*, 38(5), (Apr. 2001), 373-383.
Buniatian, Gayane, et al., "Dynamics of glial fibrillary acidic protein distribution in cultured glomerular podocytes and mesangial cells of the rat kidney", *Biology of the Cell*, 91(9), (Dec. 1999), 675-684.
Danielyan, Lusine, et al., "Colocalization of glial fibrillary acidic protein, metallothionein, and MHC II in human, rat, NOD/SCID, and nude mouse skin keratinocytes and fibroblasts", *J Invest Dermatol.*, 127(3), (Mar. 2007), 555-63.
Ghazarian, A., et al., "Memory of past exposure to the chemokine IL-8 inhibits the contraction of fibroblast-populated collagen lattices", *Exp Mol Pathol.*, 69(3), (Dec. 2000), 242-7.

(Continued)

*Primary Examiner* — Robert Mondesi
*Assistant Examiner* — Thomas J Visone
(74) *Attorney, Agent, or Firm* — Schwegman Lundberg & Woessner, P.A.

(57) ABSTRACT

The present invention relates to a method for the treatment of organs which are degenerative and/or in the pathological state by means of the use of cells, which are phenotypically stably differentiating or differentiated but not necessarily ultimately predetermined with respect to development, from a donor organ selected according to the principles of the opposite cell differentiation program (OCDP) and also to the use of cells of this type for the treatment or for the production of a drug for treatment of the same. Furthermore, the present invention relates to pharmaceutical agents comprising suitable phenotypically stable cells, cells of a first organ which is different from the second organ with respect to organ type thereby being used, which, in the normal physiological state with respect to a predetermined set of expressed genes and/or phenotypical properties, have opposite properties to the second cells in the normal physiological state.

2 Claims, 6 Drawing Sheets

(56) References Cited

OTHER PUBLICATIONS

Huang, C., et al., "Diabetic nephropathy is associated with gene expression levels of oxidative phosphorylation and related pathways", *Diabetes*, 55(6), (Jun. 2006), 1826-31.
Jeffery, D. R, "Failure of allogeneic bone marrow transplantation to arrest disease activity in multiple sclerosis", *Mult Scler.*, 13(8), (Sep. 2007), 1071-5.
Markowitz, C. E, "Interferon-beta: mechanism of action and dosing issues", *Neurology*, 68(24 Suppl 4), (Jun. 12, 2007), S8-11.
Scheibel, A. B., et al., "On the possible relationship of cortical microvascular pathology to blood brain barrier changes in Alzheimer's disease", *Neurobiol Aiging.*, 9(1), (Jan-Feb. 1988), 41-2.
Slack, J. M, et al., "Metaplasia and transdifferentiation: from pure biology to the clinic", *Nat Rev Mol Cell Biol.*, 8(5), (May 2007), 369-78.
Wobus, A. M, et al., "Embryonic stem cells: prospects for developmental biology and cell therapy", *Physiol Rev.*, 85(2), (Apr. 2005), 635-78.
"Japanese Application Serial No. 2010-525213, Office Action mailed Dec. 18, 2012", (w/ English Translation), 12 pgs.
"Chinese Application No. 200880114912.4, English Translation of Third Office Action issued Feb. 25, 2013", 13 pgs.
"Australian Application Serial No. 2008300999, Examination Report No. 1 dated May 27, 2013", 3 pgs.
"Canadian Application Serial No. 2,699,624, Office Action mailed Jul. 31, 2013", 3 pgs.
"Chinese Application No. 200880114912.4, First Office Action mailed Jun. 22, 2011", (w/ English Translation), 21 pgs.
"Chinese Application No. 200880114912.4, Fourth Office Action mailed Sep. 5, 2013", (w/ English Translation), 12 pgs.
"Chinese Application No. 200880114912.4, Second Office Action mailed Jun. 6, 2012", (w/ English Translation), 16 pgs.
"Japanese Application Serial No. 2010-525213, Office Action mailed Nov. 13, 2013", (w/ English Translation), 8 pgs.
"Russian Application Serial No. 2010114665/15(020715), Office Action dated Oct. 16, 2013", (w/ English Translation), 7 pgs.
Kim, H. S., et al., "Minocycline and neurodegenerative diseases", *Behav. Brain Res.*, 196(2), (Jan. 23, 2009), 168-179.
Liu, Yang Guoping, et al., "The role of astrocytes in multiple sclerosis", *Journal of Brain and Nervous Diseases*, 13(2), (2005), 149-150 (w/English abstract).
Petrova, P. S., et al., "Discovering novel phenotype-selective neurotrophic factors to treat neurodegenerative diseases", *Prog. Brain Res.*, 146, (2004), 167-183.
"Japanese Application Serial No. 2010-525213, Office Action mailed Mar. 18, 2014", (English Translation), 2 pgs.
"Japanese Application Serial No. 2010-525213, Response filed Apr. 28, 2014 to Office Action mailed Mar. 18, 2014", (English Translation of Claims), 1 pg.

\* cited by examiner

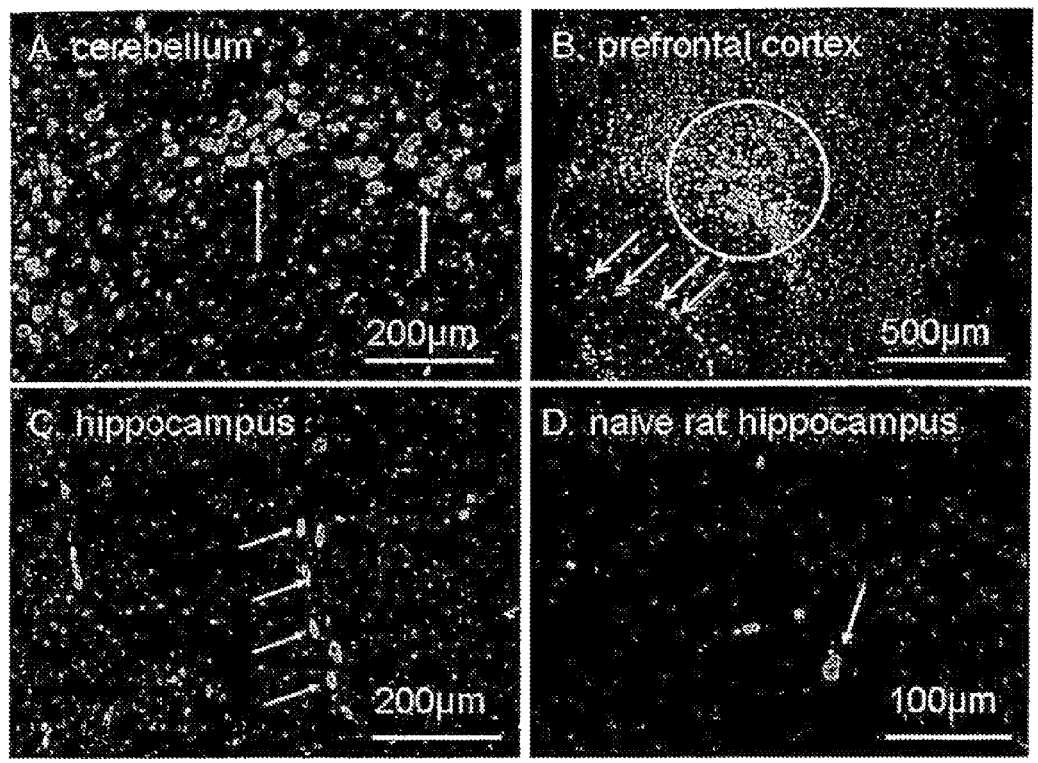
FIG. 6  Localisation of CFDA-marked HSC-T6 (green fluorescence) in the cerebellum (A), prefrontal cortex (B) and hippocampus (C) in rats with MOG-induced multiple sclerosis and in the hippocampus of the naive (without MS) rat (D).

USE OF THE OPPOSITE CELL DIFFERENTIATION PROGRAM (OCDP) FOR THE TREATMENT OF DEGENERATED ORGANS IN THE PATHOLOGICAL STATE

PRIORITY CLAIM TO RELATED APPLICATIONS

This application is a national stage application under 35 U.S.C. §371 of PCT/EP2008/003146, filed Apr. 18, 2008, and published as WO 2009/036817 A1 on Mar. 26, 2009, which claims priority to German Application No. 10 2007 044 487.9, filed Sep. 18, 2007, which applications and publication are incorporated herein by reference and made a part hereof in their entirety, and the benefit of priority is claimed thereto.

The present invention relates to a method for the treatment of organs which are degenerative and/or in the pathological state by means of the use of cells, which are phenotypically stably differentiating or differentiated but not necessarily ultimately predetermined with respect to development, from a donor organ selected according to the principles of the opposite cell differentiation program (OCDP) and also to the use of cells of this type for the treatment or for the production of a drug for treatment of the same. Furthermore, the present invention relates to pharmaceutical agents comprising suitable phenotypically stable cells.

Most of the widespread degenerative diseases of the western world are presently in the spotlight for cell-based therapies (Slack J M W. Metaplasia and transdifferentiation: from pure biology to the clinic. Nature Rev. 2007; 8: 369-378). These diseases comprise neurodegenerative diseases (Alzheimer's, Parkinson's, Huntington's etc.), chronic liver diseases (hepatitis, fibrosis and cirrhosis), diabetes, heart diseases, arthritis and many others. The fundamental concept of these cell-based therapies is to replace cells which are damaged and restricted in or have lost their regeneration capacity or to assist their replacement by trophic factors which are produced from transplanted natural or biotechnologically modified cells (Slack J M W. Metaplasia and transdifferentiation: from pure biology to the clinic, Nature Rev. 2007; 8: 369-378).

There are discussed as suitable cells for possible therapeutic success: embryonic stem cells, adult stem cells, the transdifferentiation of cells (for example haematopoietic stem cells to corresponding organ cells), and also the continuous or transitory use of cells which promote regeneration in receptor organs by production of cytokines and growth factors (Slack J M W. Metaplasia and transdifferentiation: from pure biology to the clinic, Nature Rev. 2007; 8: 369-378).

First experimental but also clinical tests in this direction have produced disappointing results (Jeffrey D R Failure of allogeneic bone marrow transplantation to arrest disease activity in multiple sclerosis. Mult. Scler. 2007; July 10 (Epub ahead of print)) and simultaneously have displayed inherent deficits in this therapeutic approach.

The concept according to the invention of the "opposite cell differentiation program" (OCDP) extends beyond the previously mentioned therapeutic approaches designed for cell replacement and pursues a different strategy.

Modern methods in cell-based therapy of chronically diseased organs are based on applications of:
1. stem cells of different origins with the property of being differentiated in cells of the diseased organ and/or
2. cells, in particular genetically manipulated cells, which have properties (e.g. the production of trophic factors), with which the regeneration of the diseased organ can be influenced positively.

Each of these methods has promised radical progress with respect to the therapeutic possibilities of chronically diseased organs or already achieved this but at the same time has entailed a series of significant and unresolved disadvantages.

In the case of stem cell therapy, pluri- or multipotent (undifferentiated) donor cells (embryonic or adult stem cells (SC), mesenchymal or epithelial haematopoietic SC, bone marrow cells, stem cells from fatty tissue and skin or hair roots and other organs) are used (Wobus A M, Boheler K R. Embryonic Stem Cells: prospects for developmental biology and cell therapy. Physiol. Rev. 2005; 85: 635-678). This application is based on findings that undifferentiated stem cells have the property of being able to convert in a limited number of cell divisions into different organ-specific differentiated cells. Examples of this are the conversion of stem cells into osteoblasts, chondrocytes, adipocytes, antigen-presenting dendritic cells. However the possibility is also discussed of converting differentiated organ cells by suitable measures— for instance by transfection of genes for transcription factors—into other differentiated organ cells (transdifferentiation; Slack J M W. Metaplasia and transdifferentiation: from pure biology to the clinic. Nature Rev. 2007; 8: 369-378). On the basis of their phenotypical flexibility (pluri- or multipotency), it is believed that stem cells could be implanted almost in all organs in order there to replace the function-bearing organ cells. The application of stem cells or transdifferentiation does however involve the following disadvantages:

- tumourigenic property (particularly in the case of embryonic stem cells)
- increased potential for dedifferentiation (with adult stem cells, generation of tumour stem cells)
- transformation into organ-foreign cells in cell culture and after transplantation
- degeneration of cells or loss of non-dispensable powers and/or regulatablity by the environment of the same on the basis of genetic manipulation
- limited quantity of obtained stem cells
- low proliferation rate of adult or already almost differentiated stem cells
- ethical scruples (in the case of embryonic and foetal stem cells)

The previous strategy of cell-based therapy of (chronically) degenerative diseases is based on the use of stem cells or other cells with therapeutic potential in the advanced stage of a disease when the spontaneous or the pharmacologically inducible protection and regeneration of intrinsic body, functional cells fails. The chronic character of the disease thereby means that, in the organ context, (pathological) regulatory systems prevail which exert an inescapable compulsion to maintain the pathology. The continuous exposition of neural and non-neural tissue with pathogenic factors triggers organ-specific homeostasis and disrupts both metabolic pathways and signal transduction routes which enable or control compensation of damage in the healthy context. These compulsions prevent (block) not only the intrinsic body regeneration but also force transplanted cells in the pathological direction. Furthermore, the pathogenic environment can accelerate the differentiation and hence the ageing and loss of function, resulting there from, of implanted stem cells. The greater the phenotypical flexibility of the stem cells used, the easier will they succumb to the pathological pressure, the greater i.e. the danger of faulty differentiation, a neoplastic disturbance or the elimination of these cells by cell death.

The aim of achieving a stable, permanently functional phenotype of the donor cells which is resistant to the degenerative environment has to date not been achieved by the use of stem cells. It is therefore the object of the present invention to avoid the known disadvantages resulting from the use of genetically modified cells and also from stem cells of different origins in the case of a cell-based therapy. This object is achieved by the methods and also the pharmaceutical agents according to the present independent claims. Advantageous embodiments are indicated in the dependent claims.

The solution to this object resides in the application of the concept of the opposite cell differentiation program (OCDP). The OCDP starts from two basic premises which are not taken into account in all other cell-based therapeutic approaches. One basic premise is the existence of cell populations (cell types) in different organs which have potentially, with respect to a specific set of expressed genes or with respect to a specific set of phenotypical properties, counter (opposite) or reciprocal properties and/or control mechanisms—there should be mentioned by way of example for instance cell populations which perform an indispensable function with respect to the maintenance of tissue homeostasis, the material transfer between different compartments (examples: blood/tissue; air/tissue), detoxification and regeneration—(abbreviated as "GPC", GFAP-producing cells) (Danielyan L, Tolstonog G, Traub P, Salvetter J, Gleiter C H, Reisig D, Gebhardt R, Buniatian G H. 4.6 Colocalization of glial fibrillary acidic protein, metallothionein, and MHC II in human, rat NOD/SCID, and nude mouse skin keratinocytes and fibroblasts. J Invest Dermatol. 2007 March; 127 (3): 555-63). The second premise is the knowledge that these cells are present in different organs in different activation states or regulation states which dominate the respective type of tissue, which generally, though not necessarily, in the case of disease assume an exactly opposite activation state (or differentiation state) or regulation state with respect to particularly important functional proteins and/or regulation mechanisms (Buniatian G. H., H-J Hartmann, P. Traub, U. Weser, H. Wiesinger, R. Gebhardt (2001). Acquisition of blood-tissue barrier supporting features by hepatic stellate cells and astrocytes of myofibroblastic phenotype. Inverse dynamics of metallothionein and glial fibrillary acidic protein expression. Neurochem. Int. 38, 373-383; Buniatian G. H., Hartmann H.-J., Traub P., Wiesinger H., Albinus M., Nagel W., Shoeman R., Mecke D., Weser U. (2002). Glial Fibrillary Acidic Protein-Positive Cells of the Kidney are Capable of Raising a Protective Biochemical Barrier Similar to Astrocytes: Expression of Metallothionein in Podocytes. *Anat. Rec.* 267, 296-306). In a novel and surprising manner, the concept of the OCDP now starts from the fact that cell transplantation orientated towards the therapy of diseased tissue is particularly successful when representatives of a cell population are transplanted, the natural activation state or phenotype of which, relative to the mentioned important antigens (proteins) or regulation mechanisms in the donor organ, is opposite to the phenotype of "related" cells in the receptor organ. It is thereby irrelevant whether the transplanted, natural cell population has stem cell properties, whether it serves as the source of trophic factors or has other properties which promote regeneration of the receptor organ. Underlying the opposite cell differentiation program is the fact that there are "related" cells in many (if not all) organs, the differentiation state of which varies in such a manner that there are organ constellations in pairs in which this differentiation state of the respective related cells can be termed counter or opposite. "Related" cells in this context does not necessarily mean related in the sense of from the same origin but can simply also mean that these cells have a limited set of the same expressed genes A, B, C, . . . so that these cells in the one organ can be characterised for example by the property: 'gene A highly expressed, gene B expressed to a small extent' and in the other by the "opposite" property: 'gene A expressed to a small extent, gene B highly expressed'. This is intended to be clarified again with reference to the two subsequent examples without restricting the invention hereto:
A) In each organ, there is a cell population which performs an indispensable function with respect to maintenance of the tissue homeostasis, the material transfer between different compartments (examples: blood/tissue; air/tissue), detoxification and regeneration (e.g. GFAP-producing cells). In addition to the intermediary filament protein GFAP (glial fibrillary acidic protein), these cells can produce at the same time other cytoskeletal proteins, for example SMAA (smooth muscle alpha-actin), a microfilament protein. Knowledge of the last few years has shown that these cells are present in various organs in different activation states which dominate in the respective type of tissue. Thus for instance astrocytes in the normal brain are characterised by high expression of SMAA and low expression of GFAP, whereas hepatic stellate cells (HSC) by a high expression of GFAP and a low expression of SMAA. This varied type of gene expression is coupled with the situation that normal astrocytes are involved in the construction of the highly impermeable blood-brain barrier, whilst the HSC cooperate in the liver in the construction of a highly permeable blood-liver tissue interface or determine this. In the case of disease, this expression state reverses respectively and hence also the permeability of the affected blood-brain tissue-barrier and also further properties with respect to maintenance of the tissue homeostasis, detoxification and regeneration. This means that, in the degenerated brain areal, the astrocytes reduce the high expression of SMAA and increase the expression of GFAP, whereas HSC in the liver reduce the expression of GFAP and increase that of SMAA. Characterisation of cells with a phenotype which is opposite in the normal state is not thereby restricted to the example of the proteins GFAP and SMAA. The therapeutic properties of GPC may be indicated by other expression patterns, as well. for instance by the expression of glutamine synthetase, metallothionein or MHC class II molecules, and determine the opposite phenotype. In this case, detoxification reactions are in the forefront of the tissue function.

B) The second example places the regulatory aspect more in the forefront. In many (if not all) adult tissues, dualism of hedgehog- and Wnt/β-catenin signal transduction is of particular importance in the substructuring of tissues: a part of the cells undergoes more the influence of hedgehog, another more that of Wnt/β-catenin. An example of this can be the intestine, in the crypts of which the Wnt/β-catenin influence predominates, whilst the hedgehog influence is dominant at the tip of the villi. Such a dualism applies even to the liver. Without the constant antagonism of these opposite signal paths, providing a certain tissue-specific metabolic balance, the tissue lapses into various types of pathology including tumour formation. In reverse, in the case of a pathology, the influence of one of these signal paths is extended at the cost of the other and hence, very similarly to the example of the GPC cited above, an opposite or reciprocal phenotype of the cells is induced but which is substantially more unstable than the respectively natural one.

The OCDP hence enables and/or presupposes the identification of suitable cells which are qualified in particular for transplantation: it is first of all determined which cell type is damaged or changed predominantly in a pathological organ or which plays the more important role originally for the pathology. It can be assumed that the pathological phenotype, with respect to essential properties, behaves opposite to its normal phenotype. This of course does not apply globally, i.e. with respect to the entire proteome of these cells but only with respect to essential properties in the above-explained sense. In a second step, an organ is identified which contains the "related" cell type which corresponds to the pathological phenotype with respect to the essential properties and if necessary shows the opposite differentiation pattern from the normal cell type of the pathological organ. The differentiating or differentiated donor cell (with opposite differentiation features) should originate from healthy donor organ with opposite physiologic functions and features of the blood-tissue interfaces, for example liver and brain. Due to experience and memory (Ghazarian A, Garner W L, Ehrlich H P. Memory of past exposure to the chemokine IL-8 inhibits the contraction of fibroblast-populated collagen lattices. Exp Mol Pathol. 2000 December; 69(3):242-7; Huang C, Kim Y, Caramori M L, Moore J H, Rich S S, Mychaleckyj J C, Walker P C, Mauer M. Diabetic nephropathy is associated with gene expression levels of oxidative phosphorylation and related pathways. Diabetes. 2006 June; 55(6):1826-31.) which the donor cell gains during the life span in donor organ after transplantation of this cell type, it can both fit into its pathological environment better and also better resist the pathogenetic pressure thereof. Consequently, the regeneration can be introduced more effectively by this cell type. It is unimportant hereby whether this cell type has specific properties of multipotent stem cells (e.g. property of transforming into related cell types of the receptor organ) or merely has regeneration-promoting properties and influences, e.g. expression of trophic factors.

In the case of the GPC the following situation occurs for example:

in the degenerated brain and in the case of regular ageing in the cell structure, astrocytes which exert a strong protective effect in the brain relative to noxious agents of the most varied of types lose their activated contractile phenotype and increasingly attain the dilated phenotype with reducing functionality. This pathological situation in the brain is improved by the supply of phenotypically stably differentiating or differentiated activated hepatic stellate cells (HSC) from liver or mesangial cells (MC) from the kidney.

For example, HSC and MC are programmed to assume the activated and contractile phenotype and, in the course of their differentiation, to intensify this phenotype increasingly (i.e. the properties of functional astrocytes). As a result of a diversity of protective factors which are produced by phenotypically stably differentiating or differentiated, activated HSC and MC (erythropoietin and/or BDNF (brain-derived neurotrophic factor) and/or metallothioneins and/or glutamine synthetase and/or NGF (nerve growth factor) and/or collagen type 1 and/or GPR 49 (G-protein-coupled receptor 49) and/or others), these cells can improve the damaged homeostasis and the survival and also the functionality of the cells of the recipient organ (in this case of the brain). Furthermore, HSC/MC, similarly to stem cells under culture conditions, can attain the properties of neurons (formation of synapses, production of neuron-specific markers, neurotransmitters and enzymes which are involved in the formation of neurotransmitters). For this reason, HSC/MC (apart from their homeostasis-improving and protective function on neurons and astrocytes) can replace the functions of lost and degenerated neurons in the case of implantation in the degenerated brain. Table 1 shows merely by way of example the amount of expression of selected factors as a function of the differentiation states of the respective cell types.

Because of the anatomical and functional mutuality ("affinity") of astrocytes, hepatic stellate cells (HSC) and mesangial cells (MC) which belong to the GFAP-positive, perivascular cells of the brain, the liver and the kidney, the latter have similar protective mechanisms against blood-born signals. The main hallmarks of degenerative diseases of the brain are the loss of neurons and profound changes in the brain-specific homeostasis, the latter being regulated by astrocytes. A feature of HSC and MC for cell based therapy of neurodegenerative diseases is that these non-neural GFAP-PC are naturally programmed to acquire and to increase in the course of their differentiation (activation), the characteristic properties of young astrocytes (anticytotoxic function), neural SC (nestin production) and neurons (β-III tubulin, neuromediators, neurotrophic factors). They proliferate rapidly in vitro and in vivo, and because of their differentiated phenotype, are maintained in a stable fashion in the diseased tissue of the recipient organ. The exactly oppositely proceeding program of differentiation of astrocytes and HSC/MC enables the use of phenotypically stable differentiating or differentiated HSC/MC for the treatment of neurodegenerative diseases.

The stably differentiating or differentiated HSC which are used for cell-based therapy of neurodegenerative diseases produce EPO (erythropoietin), GS (glutamine synthetase) and MT (metallothionein). Their cytoskeleton is supported by nestin, beta-tubulin, desmin and SMAA. In the case of these cells, GFAP, which is expressed perinuclearly or nuclearly (but not in the protrusions), can be present in small quantities.

Hence HSC and/or MC can be used for cell-based therapy in a series of neurodegenerative diseases, such as Alzheimer's disease, Parkinson disease, multiple sclerosis, stroke and other diseases characterized by loss in number and functionality of neurons and distortion of the brain-specific homeostasis.

In the case of HSC/MC (or another cell type with similar differentiation program), the cells are supplied to the diseased brain by means of implantation, intravenous administration or other types of application. The implantation of HSC can thereby be implemented even with patients with advanced stages of the above-mentioned diseases. The implantation of HSC and/or MC is intended:

1) permanently to improve the brain-specific homeostasis in damaged tissue by its pronounced detoxifying function (production of glutamine synthetase, erythropoietin, metallothionein)
2) to increase the survival rate of recipient-intrinsic neurons, and also their regeneration (e.g. axonal regeneration).
3) to improve the neurotransmission by the transformation of HSC/MC in neuron-type cells which can produce functional proteins (e.g. acetylcholine, tyrosine hydroxylase)
4) to improve the functionality of the cells in the recipient organ (the presence of HSC/MC induces the production of acetylcholine, tyrosine hydroxylase in astrocytes/neurons).
5) To increase the number of neurons according to 2), 3), 4)

In the differentiated and activated state, HSC express no MHC class II proteins and accordingly they have a very weak to scarcely present antigen-presenting function. Hence in the case of HSC implantation, the problems of rejection reaction, which are present with stem cells, and the poor survival rate of the implants is eliminated or reduced. Degeneration of the liver is characterized by loss of hepatocytes, hence decreased function of detoxification performed by hepatocytes and deep changes in liver-specific homeostasis, controlled by quiescent HSC and structural modification of liver sinusoids performed activated HSC. Quiescent HSC strongly express GFAP, an intermediate filament protein supporting the production of extracellular matrix degrading enzymes which support the facilitated blood-liver exchange via fenestration in liver capillary. Quiescent vitamin A-storing HSC produce MHC class II complex of antigens important for presentation of antigens to homing lymphocytes. Also this function is realized via liver fenestrations the size of which is controlled by quiescent HSC. Liver fibrosis is characterized by activation of HSC manifested by loss GFAP, decreased digestion of ECM proteins and development of continuous, vascular type, proper for brain capillary.

Oppositely, maturation and differentiation of astrocytes results in accumulation of large amounts of GFAP, MHC-II and metalloproteinases otherwise acquisition of features characteristic of non-differentiated HSC in healthy liver and kidney and similar cells in other non-neural organs. This set of antigens has been shown during neurodegenerative diseases (Markowitz C E. Interferon-beta: mechanism of action and dosing issues. Neurology. 2007 Jun. 12; 68(24 Suppl 4):S8-11.), Frequent occurrence of pits and lacunae in vessel walls in Alzheimer disease (Scheibel A B, Duong T. On the possible relationship of cortical microvascular pathology to blood brain barrier changes in Alzheimer's disease. Neurobiol Aging. 1988 January-February; 9(1):41-2.) demonstrate the universality of mechanisms providing the facilitated blood-tissue interaction and the capacity of GFAP-enriched perivascular cells to support the opening of paracellular avenues. The differentiation of astrocytes is terminated either in the adult brain or it can be achieved in neural cell culture.

According to the invention, differentiating and phenotypically stable differentiated astrocytes can be used for the treatment of non-neural organs undergoing fibrosis or another disease which is caused substantially by the disorder. Examples of this are cirrhosis of the liver and fibrosis of the kidneys.

Differentiated astrocytes, (or another cell type with a similar differentiation program), are supplied to the non-neural organ (for example to the liver in the case of liver fibrosis, liver cirrhosis). The use of phenotypically stably differentiating astrocytes is also possible.

In contrast to stem cell- and gene therapy, the HSC/MC-based therapies of neurodegenerative diseases and glia-based therapies of fibrosing diseases of non-neural organs (liver, kidney) offer a series of advantages.

1) Phenotypic stability of the transplanted cells and their resistance to pathological conditions which prevail in the recipient organ. The differentiated HSC/MC, after implantation in the brain, can preferably transdifferentiate into a neuron- and glia-like cell type and hence remain phenotypically stable in contrast to stem cells. This offers a crucial advantage during implantation in the diseased environment: the transplanted cells will a) not take over the phenotype of degenerated cells; and b) as a result of their natural programming and highly detoxifying function, will not only survive the toxic conditions but also will improve the homeostasis.
2) Dispensing with ethical scruples (in contrast to embryonic stem cells) and the low complexity of the isolation method. For example HSC/MC can be obtained from recipient-intrinsic (autologous) liver or kidney in larger quantities than with adult stem cells and can be multiplied in the cell culture by induction of proliferation. Other possibility is to prepare them from blood-derived mesenchyma stem cells, i.e., to induce the transformation of mesenchyma stem cells into HSC and MC.
3) The quantity of cells to be transplanted is not limited (because of their high proliferation capacity and the possibility of obtaining these cells from a donor organ).
4) Very good survival rate of implanted HSC/MC cells in the receptor tissue because of their hypoimmunogenicity. They have only a weakly pronounced (at least in cell culture conditions) antigen-presenting function since they express hardly any MHC class II proteins.

In summary, the stably differentiating or differentiated perivascular GFAP-positive cells (HSC, MC and astrocytes) respectively can offer a higher survival rate of the implant in the recipient organ, improvement in the homeostasis, phenotypical stability in the recipient organ and simple obtainment and handling of these cells before implantation.

In addition, as a further example of the application of the OCDP, the mutual replacement of the glomerular podocytes and skin keratinocytes can be mentioned.

The application of the phenotypically stably differentiating or differentiated cells is effected in the known manner. For example they can be administered or implanted intravenously, intrathecally (spinally), intracranially, intracerebroventricularly, intraperitoneally, intramuscularly and/or subcutaneously.

Application quantities are advantageously $5\times10^3$ to $1\times10^{10}$ cells. The quantity can thereby be dependent upon: 1) stage of the disease; 2) age of the patient; 3) type of disease; 3) application route (i.v., i.p. etc.); 4) application duration (chronically, once or several times); 5) preceding and/or accompanying diseases.

The application rates are advantageously single application, infusion with different infusion rates and duration, multiple or chronic application.

BRIEF DESCRIPTION OF THE DRAWINGS

FIG. 6 depicts localization of CFDA-marked HSC-T6 (green fluorescence) in the cerebellum (A), prefrontal cortex (B) and hippocampus (C) in rats with MOG-induced multiple sclerosis and in the hippocampus of the naive (without MS) rat (D).

Figure 1:
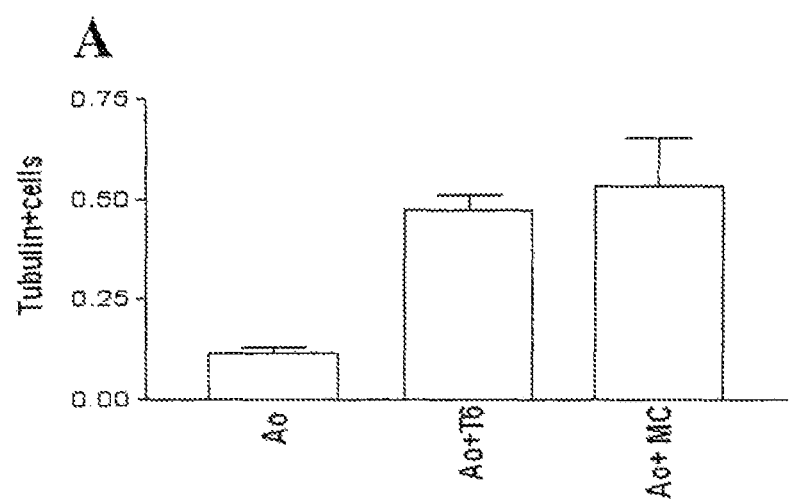
FIG. 1 shows the changes in the number of beta-III tubulin-positive cells in 14 day old astroglial cultures after co-cultivation with HSC-T6 cell line or primary MC. It is evident from the diagram that the 14 day long co-cultivation of astroglial cells (Ao) with HSC-T6 (Ao+T6) or with MC (Ao+MC) causes an almost threefold increase in the beta-III tubulin-positive cells compared with astroglial control cultures (Ao14d). On day 28, the astroglial cultures contained only few beta-III tubulin-positive cells. The administration of $5\times10^4$ HSC-T6 cells to 14 day old astroglial cultures resulted in a huge expansion in the population of beta-III tubulin-positive cells after a 7 day long co-cultivation. After 14 days in co-culture, a dramatic increase in the number of beta-III tubulin-positive cells was observed. Of these beta-III tubulin-positive cells, a large number showed a neuronal morphology, i.e. individual extended axon-like protrusions and numerous short dendrites circling the cell body. This effect was observed in cultures with a 5-fold smaller cell density. The beta-III tubulin-positive cells were organized in a network. These cells expressed beta-III tubulin to a high degree and GFAP to a very low degree.
Figure 2:
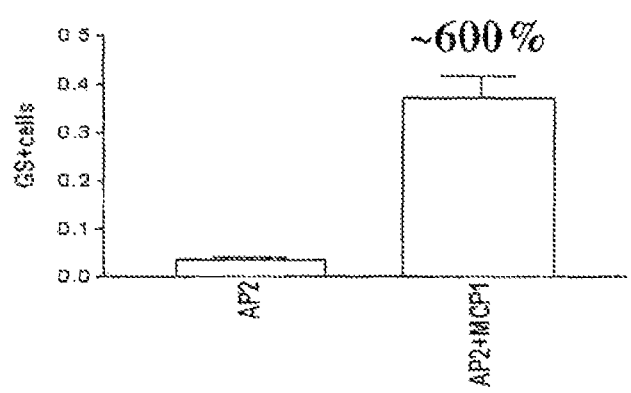
FIG. 2 shows the 600% increase in the number of GS positive cells in co-culture of astroglial cells after passage (P2) with MC (AP2+MC P1) after passage (P1) in comparison with monoculture of 56-day-old astroglial cells (AP2). Furthermore, in this illustration, the results from the comparative study of the expression of GS and MT in astroglial cultures with and without addition of HSC-T6 (the cell line of activated HSC) are represented.
Figure 3:
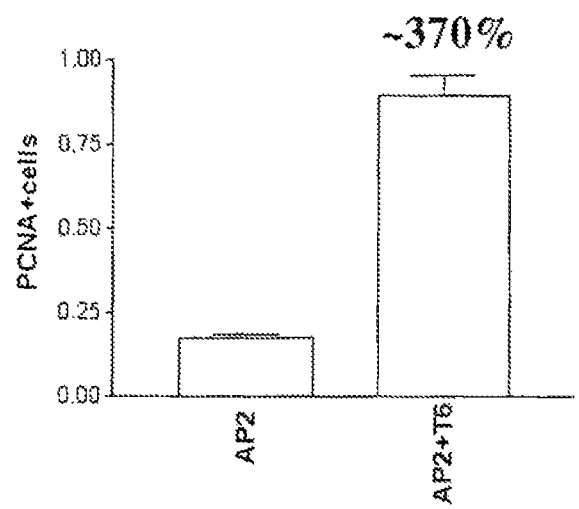
FIG. 3 shows a 370% increase in PCNA-positive cells in co-cultures of astroglial cell and 52-day-old astroglial cultures.
Figure 4:
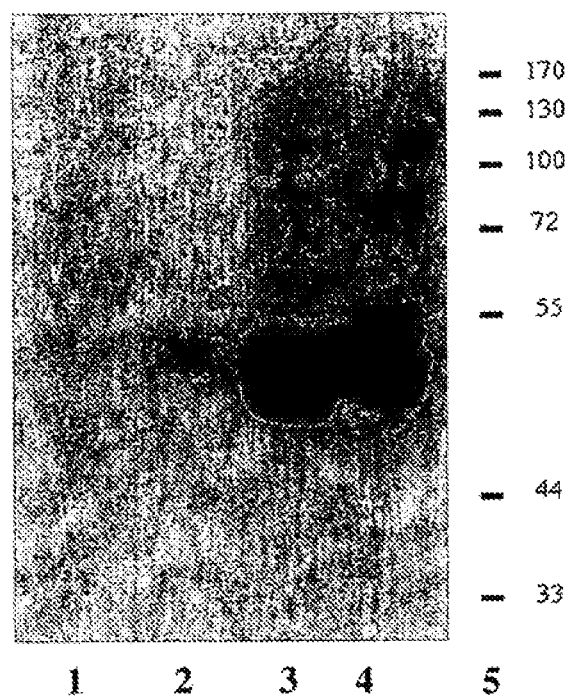
FIG. 4 demonstrates the expression of GFAP in astroglial cultures analyzed alone and in co-culture with HSC-T6 by means of Western Blot. The barely present expression of GFAP in a co-culture of astroglial cells with HSC-T6 (column 1) in comparison with the expression of GFAP in individual cultures of HSC-T6 (column 2) or astroglial primary cultures (column 3 and 4) is depicted. This indicates a very strong differentiation and hence ageing-retardant effect of HSC on astroglial cells.
Figure 5:
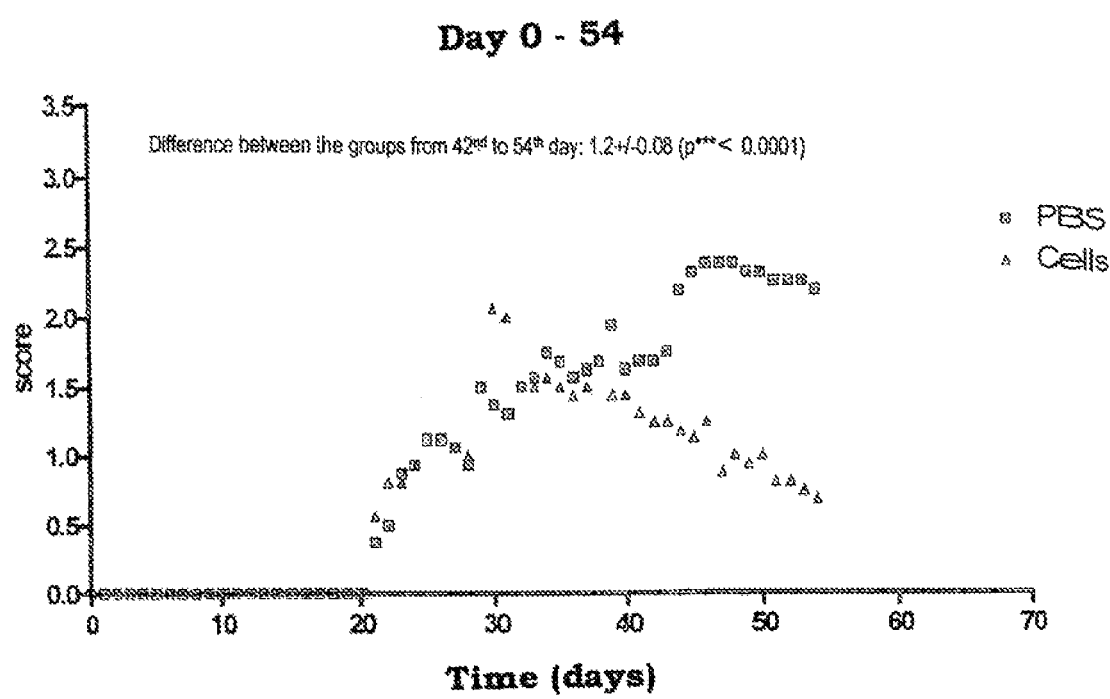
FIG. 5 lists the intermediate state of the neurological status. The group with cell treatment (green curve) had an average score of 0.9±0.05 (n=8), whereas the PBS-treated group (red curve) showed an average score of 2.21±0.06 (n=8). Hence the average of the difference between group 1 ("cells") and group 2 ("PBS") was at a score of 1.2±0.08, which implied a significant improvement in the neurological symptoms.

The subsequent examples explain the invention without restricting it hereto.

1. In Vitro Tests

The following abbreviations are used subsequently: HSC—hepatic stellate cells; MC—mesangial cells; GFAP-PC—glial fibrillary acidic protein-positive perivascular cells; AP—astroglial primary culture; P—passage; EPO—erythropoietin; GS—glutamine synthetase; MT—metallothionein; PCNA—proliferating cell nuclear antigen; OCDP—opposite cell differentiation program.

The protective properties of HSC, HSC-T6 cell line and MC were characterized in individual monocultures and co-cultures with astroglial primary cultures from the rat by means of immunocytochemical analyses of different function- and cell type-specific marker proteins. The efficiency of the OCDP treatment was evaluated in in vitro models from co-cultures of greatly differentiated primary cultures from the brain and non-neural GFAP-PC. Non-neural GFAP-PC were included in these:
1. mesangial cells from the adult kidneys and from kidneys of newborn rats
2. adult activated HSC (primary culture)
3. HSC-T6 cell line (activated HSC cell line)

All these cell types were analysed individually and in co-cultures with astroglial cells at a different culture age (up to 150 days in culture) and different quantitative conditions relative to each other and at different cell densities.

The neuron-specific, morphological and antigenic properties of non-neural differentiated GFAP-PC, i.e. activated HSC and MC, attained by means of the differentiation are shown subsequently.

Neuron- and Stem Cell-Specific Properties of GFAP-PC Cells (HSC and MC)

In the case of MC from newborn rats in cultures of different ages (day 7; day 14 and day 21) and also adult HSC and MC in different passages, a gradual reduction of GFAP and the increasing, highly regulated expression of beta-III tubulin, a marker of neurons can be observed in MC. In addition, nestin, a marker of stem cells, is highly expressed. Also adult MC and HSC express nestin and -III tubulin to a high degree. In MC, it can be observed that the expression of beta-III tubulin after 3 passages in the cell culture is extremely highly regulated.

Expression of Proteins with Detoxifying and Protective Functions (GS, MT, EPO) and Proteins which Take Part in the Neurotransmission (Synapsin and Synaptophysin) and Acetylcholine in GFAP-PC).

Adult activated HSC from the rat and MC express, to a high degree, GS, the enzyme which converts the excess of glutamate and $NH_3$ into glutamine. Metallothionein (MT) which is known for its "scavenger" function with respect to free radicals, is observed in GS-positive MC. In addition, adult differentiated HSC co-express GS and EPO. GS and EPO are also expressed in activated MC. Adult activated MC show a high proliferative capacity even after the $9^{th}$ passage. This is shown by the expression of PCNA. Activated MC also express markers of functionally active neurons: acetylcholine, synapsin and synaptophysin.

Neuron-Like Morphology of HSC and MC

Synaptic end bulbs, as are typical for neurons, were also found in MC and HSC. Also the long axon-like protrusions, typical for neurons, are formed from MC and HSC. Furthermore, the double staining for EPO and GS showed the formation of dendritic spikes in HSC.

Expression of Neuronal Markers (Beta-III Tubulin) and GFAP in Co-Cultures of HSC-T6 (HSC Cell Line) with Astroglial Primary Cultures from the Rat In order to show the efficiency of the ODCP therapy in the degenerated CNS tissue, there was used as in vitro model of neurodegeneration an astroglial primary culture which for the large part comprises astrocytes and has a very small number of neurons. This model reflects the conditions in the diseased brain in which the number of neurons drastically reduces and the number of astrocytes increases. Since astrocytes in specific brain regions have the properties of precursor cells and can serve as a source for new cell populations including neurons, cell cultures of different ages were used. In addition to young 7 day old cells and astrocytes of middle age (14 days in culture), also old astrocytes (30, 48, 90 day old cultures) were used, which lose their original properties.

Ill. 1 shows the changes in the number of beta-III tubulin-positive cells in 14 day old astroglial cultures after co-cultivation with HSC-T6 cell line or primary MC. It is evident from the diagram that the 14 day long co-cultivation of astroglial cells (Ao) with HSC-T6 (Ao+T6) or with MC (Ao+MC) causes an almost threefold increase in the beta-III tubulin-positive cells compared with astroglial control cultures (Ao14d). On day 28, the astroglial cultures contained only few beta-III tubulin-positive cells. The administration of $5 \times 10^4$ HSC-T6 cells to 14 day old astroglial cultures resulted in a huge expansion in the population of beta-III tubulin-positive cells after a 7 day long co-cultivation. After 14 days in co-culture, a dramatic increase in the number of beta-III tubulin-positive cells was observed. Of these beta-III tubulin-positive cells, a large number showed a neuronal morphology, i.e. individual extended axon-like protrusions and numerous short dendrites circling the cell body. This effect was observed in cultures with a 5-fold smaller cell density. The beta-III tubulin-positive cells were organised in a network. These cells expressed beta-III tubulin to a high degree and GFAP to a very low degree.

Expression of Neuronal Marker (Beta-III Tubulin) and GFAP in Co-Cultures of MC with Astroglial Primary Cultures from Newborn Rats The astroglial cells were co-cultivated with MC from newborn rats:
1. 14-day-old astroglial cells with MC cells freshly isolated from newborn rats and subsequent co-cultivation for 14 days.
2. 14-day-old MC with astroglial cells freshly isolated from newborn rats and subsequent co-cultivation for 14 days.
3. 14-day-old MC with 14-day-old astroglial cultures from newborn rats after a passage in culture and subsequent co-cultivation for 14 days.
4. 21-day-old astroglial cultures with 21-day-old MC from newborn rats after a passage in culture and subsequent co-cultivation for 14 days.
5. 46-day-old astroglial cells with 31-day-old MC cells in passage 1 and subsequent co-cultivation for 14 days.

In all of the 5 above-listed conditions of co-culture, the number of beta-III tubulin-positive cells was greatly increased. Furthermore, the number of silent cells, which can be detected only by nuclear staining, is, under control conditions in 60-day-old astroglial cultures, significantly higher than in co-cultures. Since the number of beta-III tubulin-positive cells in co-cultures increases greatly, it can be assumed that these silent cells are transformed into neurons.

Expression of Beta-III Tubulin in Co-Cultures of 140 Day Old Astroglial Cell Cultures and Adult HSC or MC from the Rat In this series of experiments, more than 140-day-old astroglial cultures were observed as control. The 28 day co-cultivation of 149 day old astroglial cells (AP1) with adult MC from the $8^{th}$ passage or with adult activated HSC from the $7^{th}$ passage led to the significant increase of beta-III tubulin-positive cells, compared with the control culture. Co-cultivation of AP1- and HSC-T6 cell line led to dramatic detachment of the cells from the base of the Petri dishes. The remaining adherent cell population however showed a higher number of beta-III tubulin-positive cells than in the control culture.

Anti-Cytotoxic Properties of HSC-T6

Ill. 2 shows the 600% increase in the number of GS positive cells in co-culture of astroglial cells after passage (P2) with MC (AP2+MC P1) after passage (P1) in comparison with monoculture of 56-day-old astroglial cells (AP2). Furthermore, in this illustration, the results from the comparative study of the expression of GS and MT in astroglial cultures with and without addition of HSC-T6 (the cell line of activated HSC) are represented. The addition of HSC-T6 to 52-day-old astroglial cultures led to the dramatic increase of GS, MT and desmin. The cells formed a neuron-like network with strongly configured protrusions in which a strong GS, MT and desmin expression took place.

Anti-Cytotoxic Properties of MC

The expression and correspondingly the activity of GS in 58-day-old astroglial cultures is increased dramatically by the addition of MC from newborn rats to 14-day-old co-cultures.

Development of Neuron-Specific Functions in Astroglial Co-Cultures with HSC or MC Expression of Tyrosine-Hydroxylase (TH)

On day 28, a large number of astrocytes in homogeneous culture expressed TH. After 14 days in co-culture with adult differentiated (activated) MC from primary cultures from the rat or adult differentiated HSC and MC in the $7^{th}$~$8^{th}$ passage, the number of TH-positive cells remained approximately the same in comparison with astroglial control cultures.

Expression of TH After Fairly Long Cultivation Times

On day 40 in astroglial primary cultures, the number of TH-positive cells was slightly reduced in the culture in comparison with the $28^{th}$ day. The intensity of the TH staining and the number of TH-expressing cells reduced even more greatly between the $40^{th}$ and $52^{nd}$ day. The co-cultivation of 40-day-old astroglial cultures with adult activated MC from the rat or adult activated rat-HSC, or with activated HSC-T6 cell line brought a significant increase in the TH expression in comparison with the 52-day-old astroglial control cultures.

Expression of Neurofilament Protein (NF)

The addition of 20,000 HSC-T6 cells to 14-day-old astroglial cultures resulted in a slight increase in the number of NF-expressed cells in comparison with astroglial control cultures. A 10-fold increase in the number of HSC-T6 cells led to a great increase in the number and intensity of NF-positive cells in 14 day co-cultures from AP (astrocyte-primary culture) and HSC-T6.

Expression of Proliferating Cell Nuclear Antigen (PCNA) in Co-Cultures of Astroglial Cells (Passage 2, AP2) and HSC-T6 Cell Line Ill. 3 shows a 370% increase in PCNA-positive cells in co-cultures of astroglial cell and 52-day-old astroglial cultures.

The proliferative activity of 31-day-old astroglial cells in passage 2 (AP2) was slightly reduced in comparison with primary culture with no passage (evident by means of expression of PCNA). The proliferation was greatly increased by the addition of HSC-T6 cells in AP2 and further co-cultivation for 14 days. The effect of HSC-T6 was even greater if the latter were mixed with AP2 in cell suspension and simultaneously cultivated on a Petri dish. High proliferation in mixed cultures produced a massive detachment of the cells from the base of the dish (detectable by means of large areas of densely growing cells adjacent to regions of a very dense or very sparse cell distribution). Nevertheless, in co-culture, even in the areas with a sparse cell distribution, the number of PCNA-positive cells was greater than in the astroglial culture without HSC.

Effect of HSC-T6 on the Ageing Process of Astroglial Cells

In order to clarify this effect, the expression of GFAP in astroglial cultures was analysed alone and in co-culture with HSC-T6 by means of Western Blot. Ill. 4 shows the barely present expression of GFAP in a co-culture of astroglial cells with HSC-T6 (column 1 in Ill. 4) in comparison with the expression of GFAP in individual cultures of HSC-T6 (column 2) or astroglial primary cultures (column 3 and 4). This indicates a very strong differentiation and hence ageing-retardant effect of HSC on astroglial cells.

Resistance of Astroglia and HSC-T6 Cells in Co-Culture to Hypoxia

In this series of experiments, astroglial cells were subjected to the following conditions:
1. 43-day-old cultures from the first passage (P1) were cultured alone under normoxic conditions (NC). Normoxic control
2. 43-day-old cultures of astroglial cells from the first passage (P1) were cultured for a further 10 days in NC and then transferred for a further 48 h in hypoxic conditions (HC) (1% $O_2$, 10% $CO_2$, 89% $N_2$). Hypoxic control.
3. To the 31-day-old astroglial culture in P1, were added 150,000 HSC-T6 cells and co-cultivated under NC for a further 12 days.
4. To the 31 day old astroglial culture in P1, were added 150,000 HSC-T6 cells and co-cultivated for further 10 days under NC. Subsequently, the co-culture was subjected for further 48 h to the HC.

Expression of Nestin

A moderate expression of nestin in GFAP-positive astroglial cells was observed in the first passage (AP1) under normoxic conditions. In these cultures, the nestin expression was reduced excessively under hypoxic conditions. After 12 days co-culture with HSC-T6 under NC, the expression rate of nestin was increased excessively. In 50% of the total cell population, the intensity of the nestin expression was greater than the GFAP expression. Under HC, the intensity of the staining of nestin was even higher than in control cultures of astroglial cells without HSC under NC. In co-culture of AP1 and HSC-T6 cells, the capacity to express acetylcholine was maintained, even under hypoxic conditions.

Expression of Beta-III Tubulin

The simultaneous staining of beta-III tubulin and GFAP and the individual staining with a monoclonal antibody against beta-III tubulin showed only individual beta-III tubulin-positive cells in AP1 under normoxic and hypoxic conditions. After 12 days in co-culture with HSC-T6, the number of beta-III tubulin-positive cells was significantly increased both under NC and under HC. Some of these cells showed a typically neuronal phenotype (evident by means of the presence of beta-III tubulin and the absence of GFAP). In HC, the intensity of the staining of beta-III tubulin and the number of beta-III tubulin-positive cells was the same under NC and HC but much higher than in monocultures of AP1 under NC.

Co-Expression of Glutamine Synthetase (GS) and Metallothionein (MT)

The cells under NC in monoculture of AP1 expressed GS slightly and scarcely any MT both under NC and under HC 7. After 12 days in co-culture with HSC-T6 under NC, GS and MT were highly regulated. Most cells co-expressed GS and MT. In many cells, the expression of GS or MT predominated. Under HC, the intensity of the MT staining in co-cultures was slightly less than in co-cultures under NC. Nevertheless, the expression of GS and MT in co-cultures under HC was substantially greater than in an astroglial monoculture under normoxic conditions.

Co-Expression of PCNA and Caspase 3

Only a few cells in 43-day-old astroglial cultures in the first passage (AP1) expressed PCNA under normoxic conditions (NC). Most cells also contained no caspase 3. The number of cells of AP1 cultures and the intensity of PCNA reduced further under hypoxic conditions. Co-cultivation of AP1 with HSC-T6 led to a massive increase in PCNA-positive cells under normoxic and hypoxic conditions in comparison with AP1 culture under NC and HC. The increase in proliferation in co-cultures produced a massive detachment of the cells from the base of the Petri dish which is evident by the existence of large PCNA-positive cell conglomerates and adjacent sparse, individually growing cells. In some conglomerates, the expression of caspase 3 was almost completely lacking. In others, on the other hand, a strong caspase and PCNA expression was revealed. This indicates the production of new proliferation-capable cell populations which are balanced out by apoptosis.

The present results verify the protective properties of HSC, HSC-T6 cell lines and MC on astroglial primary cultures. These properties were evaluated by means of the following parameters:
1. increased number of neurons (250-300% increase of beta-III tubulin-positive neurons) in co-cultures;
2. activation of silent cells;
3. increased expression of tyrosine-hydroxylase;
4. increased expression of GS and MT, i.e. anticytotoxic function;
5. increased cell proliferation;
6. regeneration of astrocyte population (evident by means of the increase in intensity of the nestin staining and 300% increase in nestin-positive cells);
7. expansion of the neuronal network in co-cultures;
8. increased resistance to hypoxic conditions which arise due to the following effects:
    a) increased cell proliferation under hypoxic conditions;
    b) regeneration of astroglial cultures (over 300% increase in nestin-positive cells under normoxia and hypoxia in comparison with monocultures);
    c) increased expression of GS and MT;
    d) increased number of neurons (evident by means of the 300% increase in beta-III tubulin-positive cells).

These protective properties of non-neural GFAP-positive cells are based on their long-lasting effect on CNS cells by means of:
1. production of substances which are essential for the differentiation and generation of neurons;
2. differentiation-retardant effects on astrocytes since they take over the function of differentiated astrocytes;
3. regeneration of neural cell populations by means of proliferation;
4. the intrinsic capability of transforming into neuron-like cells.

2. In Vivo Tests

Protective effect of HSC-T6 cell line for the treatment of multiple sclerosis

Test Design:

Human MOG (myelin oligodendrocyte glycoprotein) is applied intravenously in a concentration of 50 µg/animal with 18 GA rats at the age of approx. 1 month. After 24 h, the animals were divided into 2 groups: group 1 obtained 5,000,000 cells intravenously (in PBS solution), the fluorescence-marked cells being applied in the case of 2 animals from this group; group 2 (control group) obtained only PBS intravenously. Hepatic stellate cells in the form of the HSC-T6 cell line were used as cells corresponding to the OCDP. In the case of 2 animals from group 1, the fluorescence-marked cells were applied i.v. in order to detect the accessibility and the persistence of the applied cells in the CNS. These animals were prepared after 11 days. In addition, in the case of 2 normal (naive) rats in which no EAE (experimental autoimmune encephalomyelitis)-induction by MOG was induced, the same quantity of fluorescence-marked cells was applied intravenously. These control animals should have a smaller cell population of HSC-T6 in the CNS since the blood-brain barrier remained intact in these animals. The MOG-treated animals were observed daily according to the subsequent neurological "score".

Results

The animals were tested daily for striking motor features according to the following criteria:

| Score points | Score criteria |
| --- | --- |
| 1 | Hanging tail |
| 2 | Slight motor disorder of the rear legs |
| 3 | Completely lame rear legs |
| 3.5 | Spinal column immovable |
| 4 | Score 1-3.5 with additional laming of the front legs |
| 5 | Death |

The intermediate state of the neurological status is listed in illustration 5.

The entire illness was developed in the majority of the population of animals in the $10^{th}$ week after MOG application. From this time on, the group with cell application showed a significant improvement in the neurological status (score) in the further course (between day 42 to 54). The group with cell treatment (green curve in Ill. 5) had an average score of 0.9±0.05 (n=8), whereas the PBS-treated group (red curve in 111.1) showed an average score of 2.21±0.06 (n=8). Hence the average of the difference between group 1 ("cells" in Ill. 5) and group 2 ("PBS") was at a score of 1.2±0.08, which implied a significant improvement in the neurological symptoms.

Identification of the CFDA-Marked HSC-T6 in Different Brain Regions of the MS Rats and the Naive Untreated Animals In order to prove the persistence of the HSC-T6 in different brain regions with intravenous application of 5,000,000 cells, series sections of the brains of animals which obtained CFDA-marked fluorescent HSC-T6 cells, were prepared and tested by fluorescence microscopy.

Numerous cell populations were identified in the cerebellum (Ill. 6A), prefrontal cortex (Ill. 6B) and hippocampus (Ill. 6C) in MS animals, whereas only individual cells were found exclusively in the hippocampus in the case of naive rats (without MOG application) (Ill. 6D).

The above-illustrated results verify unequivocally the advantages achieved by the present invention, in particular:
1. The application of HSC-T6 cells, which have a differentiated stable phenotype, leads to a significant improvement in the neurological symptoms in the animal-experimental model of multiple sclerosis (MS);
2. The enrichment of HSC-T6 by means of intravenous administration differs significantly in the case of MS animals from naive animals with undamaged blood-brain barrier and shows that, only in the case of an advanced disease in which the blood-brain barrier is damaged, does a large number of cells migrate into the CNS, whereas only individual cells can reach the CNS with healthy animals.
3. The animals with cell application indicated no additional toxic or tumourigenic reaction to the cell application (neither healthy naive rats nor MS animals) so that the use of the cells from toxicological points of view can be considered safe.

TABLE 1

Antigenic composition of astrocytes and hepatic stellate cells (HSC) in various differentiation states

| | Expression of | | | |
|---|---|---|---|---|
| | Silent, stationary (differentiated) astrocytes Adult brain Long-term culture | Silent (undifferentiated) HSC Normal liver Short-term culture | Activated (undifferentiated) astrocytes Juvenile brain Short-term culture | Activated (differentiated) HSC Activated liver Long-term culture |
| GFAP | +++ | ++++ | −/+ | −/+ |
| SMAA | − | − | ++++ | ++++ |
| Desmin | ++ | ++ | ++++ | +++ |
| Nestin | − | − | ++++ | ++++ |
| Glutamine synthetase | −/+ | − | ++++ | ++++ |
| Metallothionein | −/+ | − | ++++ | ++++ |
| Nerve growth factor | −/+ | − | ++++ | ++++ |

SMAA Smooth muscle alpha-actin

Graduation: −, absent; +/−, absent to weak; ++, moderate; +++/high; ++++, very high

What is claimed is:

1. A pharmaceutical agent, comprising phenotypically differentiated and activated glial fibrillary acidic protein (GFAP)-positive hepatic stellate cells and adult mesangial cells of the kidney having differentiation features in terms of dynamics of GFAP-expression opposite to astrocytes, and being suitable for use in the treatment of a neurodegenerative disease and/or for the treatment of a disease which is characterized by a loss of neurons and/or for the treatment of a disease which is characterized by a loss of neuronal functionality and/or for the treatment of a neurological disease which is characterized by changes in brain specific homeostasis.

2. The pharmaceutical agent according to claim 1, wherein the disease is Alzheimer's disease, multiple sclerosis, and/or Parkinson's disease.

* * * * *